(12) United States Patent
Mellin et al.

(10) Patent No.: US 9,526,454 B2
(45) Date of Patent: Dec. 27, 2016

(54) SENSOR GUIDE WIRE COMPRISING A POLYMER LAYER

(71) Applicant: ST. JUDE MEDICAL COORDINATION CENTER BVBA, Zaventem (BE)

(72) Inventors: Lisa Mellin, Uppsala (SE); Karin Törne, Uppsala (SE)

(73) Assignee: ST. JUDE MEDICAL COORDINATION CENTER BVBA, Zaventem (BE)

( * ) Notice: Subject to any disclaimer, the term of this patent is extended or adjusted under 35 U.S.C. 154(b) by 356 days.

(21) Appl. No.: 13/800,142

(22) Filed: Mar. 13, 2013

(65) Prior Publication Data

US 2013/0261435 A1    Oct. 3, 2013

Related U.S. Application Data

(60) Provisional application No. 61/616,516, filed on Mar. 28, 2012.

(51) Int. Cl.
*A61B 5/00* (2006.01)
*A61M 25/00* (2006.01)
(Continued)

(52) U.S. Cl.
CPC .......... *A61B 5/6851* (2013.01); *A61B 5/0215* (2013.01); *A61B 6/12* (2013.01); *A61M 25/09* (2013.01);
(Continued)

(58) Field of Classification Search
CPC .... A61B 5/0215; A61B 5/6851; A61M 25/09; A61M 2025/0002; A61M 2025/09166; A61M 2025/09175; A61M 2025/09075; A61M 2025/09133; A61M 2025/0915; A61M 2025/0046
See application file for complete search history.

(56) References Cited

U.S. PATENT DOCUMENTS 5,368,048 A    11/1994    Stoy et al.
5,873,835 A *   2/1999    Hastings ............... A61B 5/0215
                                                                  600/488
(Continued)

FOREIGN PATENT DOCUMENTS

EP    1 927 316 A1    6/2008
JP    2004-230142 A    8/2004
(Continued)

OTHER PUBLICATIONS

International Search Report and Written Opinion, Jul. 30, 2013, 11 pages.
(Continued)

*Primary Examiner* — Devin Henson
(74) *Attorney, Agent, or Firm* — Foley & Lardner LLP

(57) ABSTRACT

A sensor guide wire for an intravascular measurement of at least one physiological or other variable in a living body may have a proximal region, a distal sensor region, and a tip region. The sensor guide wire may further comprise a sensor element arranged in the sensor region, and comprising a sensor portion for measuring the variable and to generate a sensor signal in response to the variable. Furthermore, a core wire, having a longitudinal axis A, and comprising at least a tip core wire portion, extends essentially along the tip region of the sensor guide wire. The tip core wire portion may further comprise a distal tip. At least a major part of the tip core wire portion is provided with a polymer layer essentially enclosing the at least major part. The distal tip of the tip core wire portion may further comprise an enlargement.

34 Claims, 3 Drawing Sheets

(51) Int. Cl.
  *A61B 6/12* (2006.01)
  *A61B 5/0215* (2006.01)
  *A61M 25/09* (2006.01)

(52) U.S. Cl.
  CPC ........... *A61M 2025/0002* (2013.01); *A61M 2025/0046* (2013.01); *A61M 2025/0915* (2013.01); *A61M 2025/09075* (2013.01); *A61M 2025/09133* (2013.01); *A61M 2025/09166* (2013.01); *A61M 2025/09175* (2013.01)

(56) References Cited

U.S. PATENT DOCUMENTS

| | | | | |
|---|---|---|---|---|
| 6,142,958 | A * | 11/2000 | Hammarstrom | A61B 5/6851 600/486 |
| 6,167,763 | B1 | 1/2001 | Tenerz et al. | |
| 6,248,083 | B1 | 6/2001 | Smith et al. | |
| RE39,863 | E | 10/2007 | Smith | |
| 7,747,314 | B2 * | 6/2010 | Parins | A61M 25/09 600/433 |
| 7,824,345 | B2 | 11/2010 | Euteneuer et al. | |
| 8,968,215 | B2 | 3/2015 | Murayama et al. | |
| 2001/0009980 | A1 * | 7/2001 | Richardson | A61M 25/09 600/585 |
| 2004/0039308 | A1 | 2/2004 | Murayama et al. | |
| 2004/0225232 | A1 * | 11/2004 | Malmborg | A61B 5/0215 600/585 |
| 2007/0255145 | A1 * | 11/2007 | Smith | A61B 5/0215 600/485 |
| 2007/0299366 | A1 * | 12/2007 | Sharrow | A61M 25/09 600/585 |
| 2008/0255446 | A1 * | 10/2008 | Akins | A61B 5/06 600/424 |
| 2011/0152721 | A1 | 6/2011 | Sela et al. | |
| 2012/0203207 | A1 * | 8/2012 | Northrop | A61M 25/09 604/529 |

FOREIGN PATENT DOCUMENTS

| | | |
|---|---|---|
| JP | 2007-515259 A | 6/2007 |
| WO | WO-95/26678 A1 | 10/1995 |
| WO | WO-99/19018 A2 | 4/1999 |
| WO | WO-2005/063329 A1 | 7/2005 |
| WO | WO 2009/054800 A1 | 4/2009 |
| WO | WO-2009/054802 A1 | 4/2009 |

OTHER PUBLICATIONS

International Preliminary Report on Patentability, PCT/IB2013/000853, Oct. 9, 2014, 8 pages.

* cited by examiner

US 9,526,454 B2

SENSOR GUIDE WIRE COMPRISING A POLYMER LAYER

This application claims priority from U.S. Provisional Application 61/616,516, filed Mar. 28, 2012, incorporated herein by reference in its entirety.

BACKGROUND

The present invention relates to a sensor guide wire, and in particular to a sensor guide wire provided with a polymer layer in the tip region.

Today, there is an increased need for invasive measurements of physiological variables. For example, when investigating cardiovascular diseases, it is strongly desired to obtain local measurements of blood pressure, flow and temperature in order to evaluate the condition of the subject under measurement. Therefore, methods and devices have been developed for disposing a miniature sensor inside the body of an individual at a location where the measurements should be performed, and for communicating with the miniature sensor in order to provide the physician or medical technician with critical information as to the status of a patient's condition. Typically, the miniature sensor is arranged at a distal end of a guide wire, which is generally known in the art, and used for example in connection with the treatment of coronary disease.

The distal end of the guide wire is inserted into the body of a patient, for example into an opening of the femoral artery, and placed at a desired location. Once the guide wire is placed by the physician into the appropriate location, e.g. in a coronary artery, the miniature sensor can measure the blood pressure and/or flow. The measurement of blood pressure is a way to diagnose e.g. the significance of a stenosis. For evident reasons, the dimensions of the sensor and the guide wire are fairly small; the guide wire typically has a diameter of 0.35 mm. Generally, the sensor element is in the form of an elongated, essentially rectangular chip with a pressure sensitive member in the form of a membrane provided thereon.

In order to power the sensor and to communicate signals representing the measured physiological variable to a control unit acting as an interface device disposed outside the body, one or more microcables for transmitting the signals are connected to the sensor, and are routed along the guide wire to be passed out from the vessel to an external control unit via a connector assembly. Most commonly, extremely thin electrical cables are provided inside the guide wire, which itself is provided in the form of a tube (having an outer diameter of e.g. 0.35 mm), oftentimes made of stainless steel. In order to increase the bending strength and maneuverability of the tubular guide wire, a core wire is positioned inside the tube. The mentioned electrical leads are positioned in the space between the inner lumen wall of the tube and the core wire. Furthermore, the sensor chip is often arranged in a short tube, also referred to as a jacket or a sleeve. The jacket is hollow and accommodates, besides the sensor chip, a portion of a core wire and often at least one microcable. Furthermore, a first coil may be attached to the distal end of the jacket, and optionally a second coil may be attached to the proximal end of the jacket. The first and second coils may be attached to the respective end of the jacket, e.g. by gluing, or alternatively soldering. The purpose of the first coil is to provide a tip with high flexibility. In addition, the distal coil is often designed to be radioopaque, to enable the user to locate the tip on an angiogram during use.

A large flexibility of the sensor guide wire is advantageous in that it allows the sensor guide to be introduced into small and tortuous vessels. It should, however, also be recognized that if the core wire is too flexible, it would be difficult to push the sensor guide forward into the vessels, i.e. the sensor guide wire must possess a certain "pushability" and a certain "torquability." Additionally, the sensor guide must be able to withstand the mechanical stress exerted on the core wire especially in sharp vessel bends.

Several different designs of sensor guide wires are known in the prior art, and examples of such sensor guide wires are disclosed in U.S. Pat. No. 6,167,763 B1, which describes the cantilevered mounting of the sensor element, US RE39863 E1, which discloses the sensor element, and U.S. Pat. No. 6,248,083 B1, showing the complete sensor guide wire assembly, which all are assigned to the assignee of the present application, and which are hereby all incorporated by reference for the devices and methods described therein.

A further example of a sensor guide wire is disclosed in WO 2009/054800 A1, assigned to the present assignee. The sensor guide wire has a proximal shaft region, a flexible region, a distal sensor region, and a tip region. The tip region of the sensor guide wire is provided with a tip core wire at least partly enclosed by a distal coil.

Besides being flexible enough, it can be also important that the sensor guide wire tip responds when steering the sensor guide wire through the tortuous vessels, i.e. the sensor guide wire tip must also have sufficient "steering response." "Steering response" is a measure of the irregular behavior of a sensor guide wire when the sensor guide wire tip is subjected to a non-linear pathway and rotated. This rotation is initiated by the user at the proximal end of the assembly, and depending on the characteristics of the different sections of the assembly, will be transferred along the wire in slightly different ways. The "steering response" of a sensor guide wire tip is a general property of the distal tip components.

The inventors of the present invention has further identified a need for a sensor guide wire with improved properties relating to the possibilities for the physician to feel constrictions and various bends and turns in the vessels when introducing the sensor guide wire. Thus, there is a need for a sensor guide wire which provides improved "sensing capabilities."

SUMMARY

An object of the present invention is to achieve a sensor guide wire which is easier to introduce into small and tortuous vessels than prior art sensor guide wires.

A further object of the present invention is to provide a sensor guide wire with improved "sensing capabilities," i.e. which facilitates for the physician to feel constrictions and plaque, and accordingly, facilitates maneuvering through the various bends and turns in the vessels.

Still another object of the present invention is to provide a sensor guide wire which is easy to position correctly in the vessel.

According to one aspect of the present invention, the above mentioned objects can be achieved by a sensor guide wire comprising a polymer layer in the tip region.

According to a further aspect of the present invention, the above mentioned objects are achieved by a sensor guide wire comprising a polymer layer in the tip region which is radioopaque.

In accordance with an embodiment of the present invention, the sensor guide wire, used for intravascular measurements of at least one physiological or other variable in a living body, has a proximal region, a distal sensor region and a tip region.

The sensor guide wire further comprises, a sensor element arranged in the sensor region, and comprising a sensor portion, for measuring the variable and to generate a sensor signal in response to the variable. A core wire, having a longitudinal axis A, and comprising at least a tip core wire portion, extends essentially along the tip region of the sensor guide wire.

The tip core wire portion further comprises a distal tip, and at least a major part of the tip core wire portion is provided with a polymer layer essentially enclosing the at least major part.

The sensor guide wire according to one embodiment of the present invention provides a smoother surface, which does not hinder advancement of the sensor guide wire in the tortuous vessels.

An embodiment of the present invention may further provide a sensor guide wire which comprises a clearly visible radioopaque tip portion which facilitates the positioning of the sensor guide wire in the vessels.

According to a further aspect of the present invention, the distal tip of the tip core wire portion of the sensor guide wire may be provided with an enlargement. The enlargement facilitates a secure attachment of the polymer layer and reduces the forces that the layer is subjected to. Furthermore, the enlargement improves the "sensing capabilities."

It is to be understood that both the foregoing general description and the following detailed descriptions are exemplary and explanatory only, and are not restrictive of the invention as claimed.

BRIEF DESCRIPTION OF THE DRAWINGS

The features, aspects and advantages of the present invention will become apparent from the following description, appended claims, and the accompanying exemplary embodiments shown in the drawings, which are briefly described below.

FIG. 5b shows a front view of the tip core wire portion shown in FIG. 5a.

DETAILED DESCRIPTION

Figure 1:
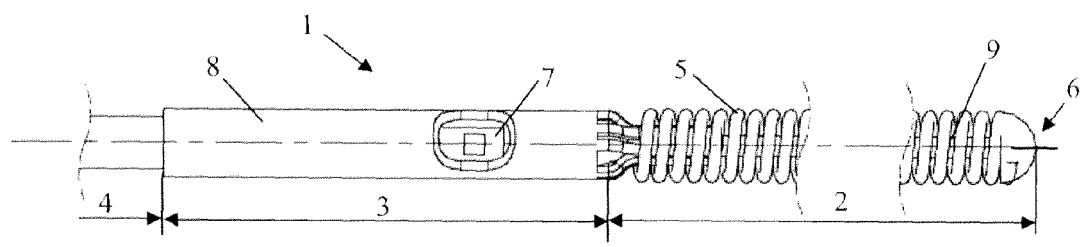
FIG. 1 shows parts of the distal portion of a conventional sensor guide wire.

FIG. 1 shows parts of a conventional sensor guide wire 1. The sensor guide wire 1 has, in the drawing, been divided into three sections (2-4) for illustrative purposes. The section 2 is the most distal portion of the sensor guide wire, i.e. that portion which is going to be inserted farthest into the vessel, and section 4 (only partly shown) is the most proximal portion, i.e. that portion being situated closest to a not-shown male connector. The male connector is adapted to be disposed outside the body, and connected to a female connector. A wired connection is thereby provided between a sensor element 7 provided in the sensor region 3 and the male connector. The wired connection provides a supply voltage from the control unit to the sensor and transfers a signal between the internal sensor and the external connectors. The female connector may, in turn, be connected wirelessly or by wired connection to an external communications unit for processing of the sensor signal.

The distal portion 2 comprises a radioopaque coil 5, which may be made of e.g. platinum, provided with an arced tip 6. In the distal portion 2, there is also attached a solid metal core wire 9 which is enclosed by the radioopaque coil 5. The sensor guide wire 1 further comprises a sensor element 7, enclosed by a jacket 8, provided in the sensor region 3, for measuring the physiological variable and to generate a sensor signal in response to the variable. Furthermore, at least one micro cable (not shown) running along the length of the sensor guide wire 1 is connected to the sensor element 7.

Figure 2:
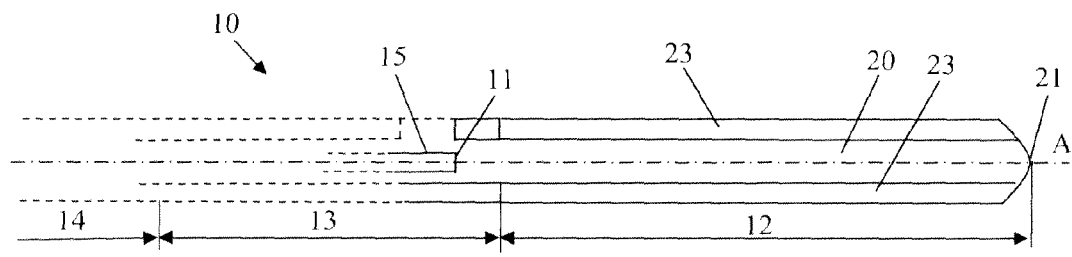
FIG. 2 shows a schematic longitudinal cross sectional view of a distal portion of a sensor guide wire, the distal portion comprising a polymer layer according to one embodiment of the present invention.

With reference to FIG. 2, a longitudinal cross section of a portion of a sensor guide wire 10 for intravascular measurements of at least one physiological or other variable in a living body, is shown. The sensor guide wire 10 has a proximal region 14 (partly shown), a distal sensor region 13 and a tip region 12. The sensor guide wire 10 comprises a sensor element 11 arranged in the sensor region 13, and comprising a sensor portion 15, for measuring the variable and to generate a sensor signal in response to the variable. Furthermore, the sensor guide wire 10 comprises a core wire 18, having a longitudinal axis A, and comprising at least a tip core wire portion 20, extending essentially along the tip region 12 of the sensor guide wire 10. The tip core wire portion 20 further comprises a distal tip 21 at the distal end of the sensor guide wire 10. At least a major part of the tip core wire portion 20 is provided with a polymer layer 23 essentially enclosing the at least major part. Providing the sensor guide wire 10 with a polymer layer 23, being arranged as the outermost layer, in the tip region 12 is advantageous in comparison to a sensor guide wire provided with a distal coil, as shown in FIG. 1, since the polymer layer 23 provides for a smoother outer surface 24 in the tip region 12. The smooth outer surface facilitates crossing coronary lesions.

Figure 3:
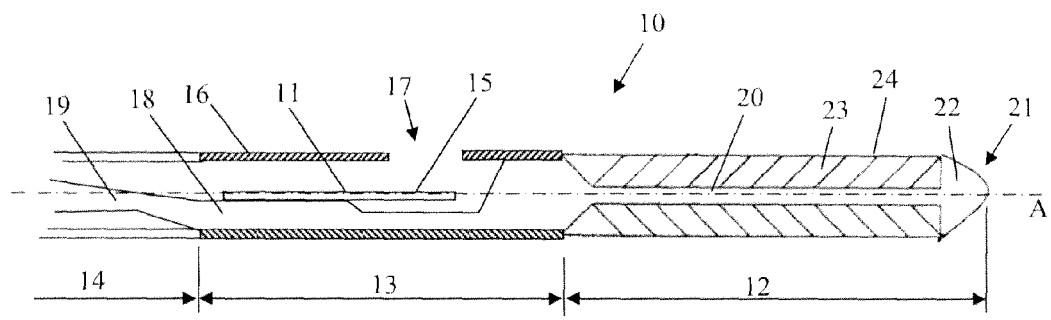
FIG. 3 shows a schematic longitudinal cross sectional view of a distal portion of a sensor guide wire, the distal portion comprising a polymer layer and an enlargement according to one embodiment of the present invention.

According to another embodiment, as illustrated in FIG. 3, the distal tip 21 of the tip core wire portion 20 is provided with an enlargement 22. The enlargement 22 provides for improved "sensing capabilities," due to the difference in friction of the polymer layer 23 and the distal tip provided with the enlargement.

Furthermore, as illustrated in FIG. 3, the sensor guide wire may be provided with a jacket 16, adapted to enclose at least a part of the sensor element 11, and being provided with at least a first sensor opening 17. However, according to another embodiment, the sensor guide wire instead may be provided with an elongated tube which extends at least along the sensor region 13 and at least partly along the proximal region 14. The elongated tube encloses at least a part of the sensor element 11 and is preferably provided with at least a first sensor opening 17.

According to one embodiment, as also illustrated in FIG. 3, the core wire 18 further comprises a proximal core wire portion 19, extending at least partly along the proximal region 14.

Figure 4:
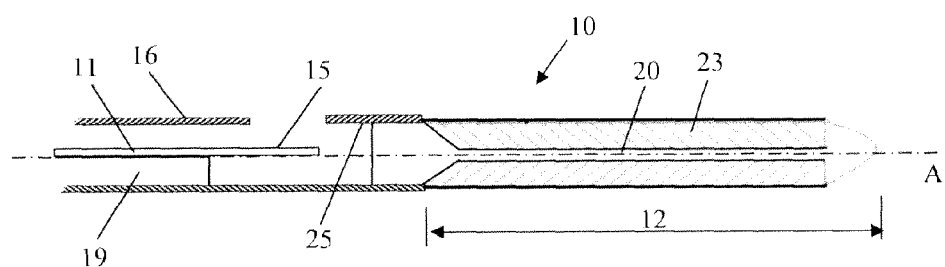
FIG. 4 shows a schematic longitudinal cross sectional view of the distal portion of the sensor guide wire, according to one embodiment of the present invention.

FIG. 3 further illustrates that the core wire 18 may extend continuously along the proximal region 14, the sensor region 13 and the tip region 12. However, the core wire 18 may, according to another embodiment, comprise a proximal core wire portion 19 and a tip core wire portion 20 being two spatially separate parts, each part being attached to the jacket 16, as illustrated in FIG. 4. As shown in FIG. 4, the tip core wire portion 20 is partly inserted into the jacket 16 and attached to an inner surface 25 of the jacket 16. Preferably, the sensor element 11 is attached to the proximal core wire portion 19, and mounted in a cantilevered way. The term "cantilevered" means that one end of the sensor element 11 is rigidly mounted, e.g. to the proximal core wire portion 19 and the opposite end, provided with the sensor portion 15, of the sensor element 11 protrudes from the site of the mounting into a medium that is substantially less rigid than that at the mounting site.

As illustrated in FIG. 4, the polymer layer 23 encloses a major part of the entire length of the tip region 12. Preferably, the major part is at least 75% of the entire length of the tip core wire portion 20. However, the polymer layer 23 may enclose between 50-100% of the entire length of the tip core wire 20. Thus, the entire tip core wire portion 20 may be provided with the polymer layer 23. In one embodiment, the distal half of the tip core wire portion 20 is provided with the polymer layer 23. Providing the major part of the tip core wire portion 20 with a polymer layer 23, and in particular the distal half of the tip core wire portion 20, facilitates advancement of the sensor guide wire 10 in the tortuous vessels.

According to one embodiment, the polymer layer 23 essentially encloses the tip core wire portion 20. Preferably, the polymer layer 23 encloses the tip core wire portion 20 entirely, thus, the polymer layer 23 preferably extends continuously around the circumference of the tip core wire portion 20. However, in another embodiment, the polymer layer 23 may be arranged to partially enclose the tip core wire portion 20. Thus, the polymer layer 23 may be arranged to enclose only parts of the tip core wire portion 20 around the circumference of tip core wire portion 20. Preferably, the thickness of the polymer layer 23 is approximately 0.1 mm. However, the polymer layer 23 may have any other thickness as long as the diameter of the sensor guide wire in the tip region 12 does not exceed 0.35 mm. The thickness of the polymer layer may be between 0.01 and 0.17 mm. In one embodiment, the thickness of the polymer layer 23 varies along the tip core wire portion 20 in the tip region 12.

Figure 5A:
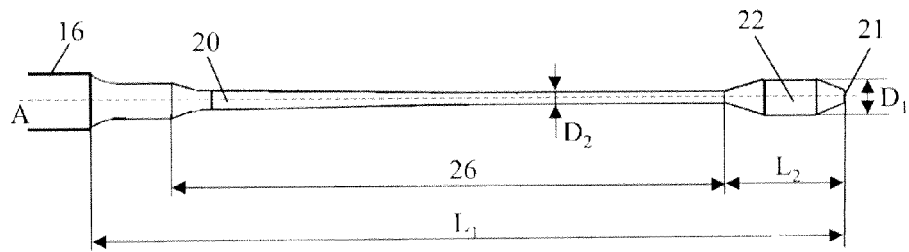
FIG. 5a shows a schematic view of a tip core wire portion comprising an enlargement at the distal tip, according to one embodiment of the present invention.
Figure 5B:
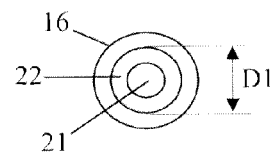

FIG. 5a illustrates the tip core wire portion 20 according to one embodiment of the present invention. The length $L_1$ of the tip core wire portion 20 is preferably between 25 mm and 35 mm, and more preferably between 28 mm and 32 mm. The enlargement 22, provided at the distal tip 21, has a circular cross-section, with a diameter $D_1$, in a plane perpendicular to the longitudinal axis A, as shown in FIG. 5b. The diameter $D_1$ of the enlargement is preferably between 0.01 and 0.35 mm.

According to one embodiment, the diameter $D_1$ is larger than a diameter $D_2$ of an intermediate portion 26 of the tip core wire portion 20, thereby an enlargement 22 is provided. The diameter $D_2$ of the intermediate portion 26 may be between 0.01 and 0.25 mm, and more preferably between 0.02 and 0.1 mm. The intermediate portion 26 may be tapering towards the distal tip 21 or may have uniform thickness along the longitudinal axis A. As also mentioned above, the diameter of the sensor guide wire in the tip region 12 can be as a maximum 0.35 mm. Accordingly, the diameter of the intermediate portion 26 and the polymer layer 23 can be as a maximum 0.35 mm in total. It can also be less than 0.35 mm, depending on the desired stiffness of the tip, and the choice of polymer layer material. According to one embodiment, the polymer layer 23 is applied to the tip core wire portion 20 and subsequently ground down, such that the diameter of the sensor guide wire in the tip region 12 is 0.35 mm or less than 0.35 mm.

When applying the polymer layer 23 to the tip core wire portion 20 of the guide wire 10 it can be crucial that the polymer layer 23 is firmly attached to the underlying tip core wire portion 20. Thus, in one embodiment, the polymer layer is attached to the tip core wire portion 20, and preferably to the intermediate portion 26 of the tip core wire portion 20. This is advantageous in that the enlargement 22 protects the polymer layer 23 from the force acting on the polymer layer caused by the blood flow. In another embodiment, this is accomplished by attaching the polymer layer 23 to the enlargement 22, which is provided with a larger diameter $D_1$ compared to diameter $D_2$ of the intermediate portion 26 of the tip core wire portion 20. Thereby a secure attachment of the polymer layer 23 is achieved and the forces that the polymer layer 23 is subjected to are reduced.

In the embodiment shown in FIGS. 5a and 5b, the enlargement 22 is tapering distally along the longitudinal axis A towards the distal tip 21. The enlargement 22 is further tapering proximally along the longitudinal axis A towards the intermediate portion 26. The taper could be stepwise or a gradual continuous taper. The diameter $D_1$ is larger than the diameter $D_2$ of the intermediate portion 26 of the tip core wire portion 20, the ratio is preferably $$\frac{D_1}{D_2} > 1.2.$$

The length $L_2$ of the enlargement 22 may be less than 5 mm, more preferably between 0.2 and 1.6 mm.

Figure 6:
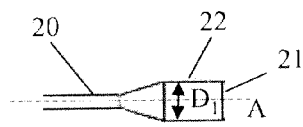
FIG. 6 shows the enlargement of the distal tip according to another embodiment of the present invention.

According to another embodiment, as illustrated in FIG. 6, the diameter $D_1$ of the enlargement 22 of the tip core wire portion 20 is uniform along the longitudinal axis A closest to the distal tip 21. Thus, as seen in FIG. 6, the enlargement 22 has a blunt end.

In another embodiment, the enlargement 22 is shaped essentially as a truncated cone. However, according to another embodiment of the present invention, the enlargement 22 may be shaped essentially as a hemisphere.

The polymer could be any biocompatible polymer and the polymer could be a homopolymer or copolymer. The co-polymer could be a random, alternating, statistic or a graft co-polymer derived from two or more monomers. The polymer can comprise for example a polyester, polyether, polyamide, polyamine, polyacrylate, polyalkene, polyurethane, polyurethane urea, polysiloxane, polycarbonate, SEBS rubber, polypropylene or co-polymers or mixtures thereof. Co-polymers could be, but are not limited to, for example polyester-co-ether, or polyester-co-urethane, or polyether-co-polyurethane, or polyester-co-polyamide or polyether-co-polyamide, or polyether-co-polyester-co-polycarbonate. The surface of the polymer layer 23 can be modified to adapt the frictional characteristics of the surface. This can be achieved by coating, plasma treatment, corona treatment, surface grafting, photo-oxidation, chemical treatment and other methods known in the art.

According to one embodiment, the polymer layer 23 is radiopaque. The radiopaque polymer layer 23 facilitates positioning of the tip region 12 of the sensor guide wire 10 in the vessel as it is visible on an angiogram.

According to one embodiment, the polymer layer 23 comprises a radiopaque filler. Thus, the X-ray opacity is then achieved by mixing an X-ray opaque filler with the polymer before applying the polymer layer 23 in the tip region 12. The radioopaque filler is preferably a ceramic or metal powder such as any of, or a combination of, bismuth, barium, tungsten, tantalum, platinum, hafnium, gold, zirconium, their oxides or similar element suitable to achieve a radioopaque polymer layer 23.

According to another embodiment, the X-ray opacity is achieved by a polymer layer 23 comprising iodine. In this case, the iodine is not a filler but covalently hound to the polymer.

In one embodiment, the polymer layer 23 is a hollow polymer tube enclosing the tip core wire portion 20 and extending along the longitudinal axis A in the tip region 12.

In one embodiment, the polymer tube is heated and formed or shrunk onto the tip core wire portion 20. However, the polymer layer 23 may be dip coated or injection molded onto the tip core wire portion 20.

Figure 7:
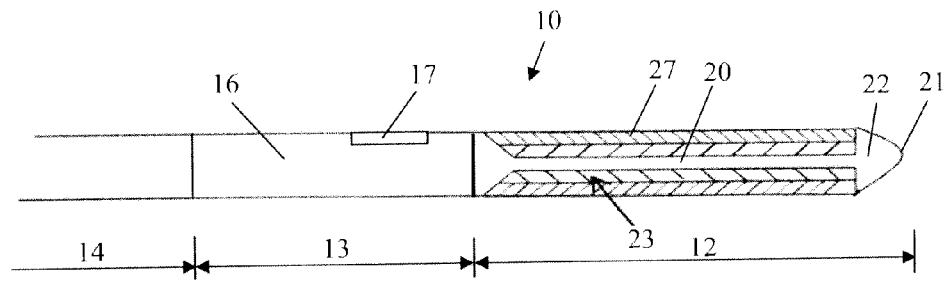
FIG. 7 shows a schematic view of the proximal region and the distal sensor region, and a longitudinal cross sectional view of the tip region provided with a polymer layer and a outer tube, according to one embodiment of the present invention.

According to another embodiment of the present invention, FIG. 7 is a partial longitudinal cross sectional view of the distal part of the sensor guide wire 10, wherein a longitudinal cross section of the tip region 12 is shown. In the embodiment shown in FIG. 7, the polymer layer 23 comprises a higher degree of radiopaque filler than in the embodiments shown in FIGS. 2-4. Preferably, the polymer layer 23 comprises a polymer with >60 wt % radiopaque filler, such that the polymer layer 23 gives high x-ray contrast. According to this embodiment, an outer tube 27 is provided that encloses the polymer layer 23. The outer tube 27 acts as a protective layer on top of the polymer layer 23. The outer tube 27 may be a polyolefin, fluoropolymer, or silicone elastomer, or similar material. In one embodiment, the outer tube 27 is a heat shrinking tube.

According to one embodiment, an adhesive material is arranged between the tip core wire portion 20 and the polymer layer 23. The adhesive material (primer) may be added between parts of the tip core wire portion 20 and the polymer layer 23 to ensure a good adherence between the tip core wire portion 20 and the polymer layer 23.

The polymer layer 23 may comprise a ceramic or metal powder such as any of, or a combination of, bismuth, barium, tungsten, tantalum, platinum, their oxides or similar element suitable to achieve a radiopaque polymer layer 23. The ceramic or metal powder may be applied onto the polymer layer 23 as a coating or may be mixed into the polymer as a radiopaque filler, as mentioned above. According to one embodiment, the ceramic or metal powder is mixed into the polymer as a radioopaque filler and, in addition, the core wire 20 is coated with a thin layer of metal such as, gold or platinum which is then coated with a polymer comprising ceramic or metal powder. The metal coating allows a lower filler content in the polymer.

In yet another embodiment, the polymer layer 23 comprises a nanocomposite hybrid material, preferably synthesized by a sol-gel method. Preferably, the nanocomposite hybrid material comprises $Ta_2O_5$.

In the field of guide wires, which is a different technical field, it is known to provide a guidewire with a polymer sleeve. The polymer sleeve provides a more lubricous surface. For example, in U.S. Pat. No. 5,368,048 A, a method of making a radioopaque tipped, sleeved guidewire is disclosed. The sleeve is formed of a polymer composition. Furthermore, in US 2007/0299366 A1, a guidewire comprising a core wire and a polymer jacket attached to the core wire is disclosed.

Besides those embodiments depicted in the figures and described in the above description, other embodiments of the present invention are also contemplated. For example, any single feature of one embodiment of the present invention may be used in any other embodiment of the present invention. For example, the following is a list of embodiments, but the invention should not be viewed as being limited to these embodiments.

(I) Sensor guide wire (10) for intravascular measurements of at least one physiological or other variable in a living body, which sensor guide wire (10) has a proximal region (14), a distal sensor region (13) and a tip region (12), the sensor guide wire (10) comprising:

a sensor element (11) arranged in said sensor region (13), and comprising a sensor portion (15), for measuring said variable and to generate a sensor signal in response to said variable;

a core wire (18), having a longitudinal axis A, and comprising at least a tip core wire portion (20), extending essentially along said tip region (12) of said sensor guide wire (10);

wherein said tip core wire portion (20) further comprises a distal tip (21), wherein at least a major part of said tip core wire portion (20) is provided with a polymer layer (23) essentially enclosing said at least major part.

(II) Sensor guide wire according to embodiment I, wherein said distal tip (21) of said tip core wire portion (20) is provided with an enlargement (22).

(III) Sensor guide wire according to any of embodiments I-II, wherein said major part is at least 75% of the entire length $L_1$ of said tip core wire portion (20).

(IV) Sensor guide wire according to any of embodiments I-III, wherein the distal half of said tip core wire portion (20) is provided with said polymer layer (23).

(V) Sensor guide wire according to any of embodiments I-IV, wherein the entire tip core wire portion (20) is provided with said polymer layer (23).

(VI) Sensor guide wire according to embodiment III, wherein the length $L_1$ of the tip core wire portion (20) is preferably between 25 mm and 35 mm, more preferably between 28 mm and 32 mm.

(VII) Sensor guide wire according to any of embodiments II-VI, wherein said enlargement (22) has a circular cross-section, with a diameter D1, in a plane perpendicular to said longitudinal axis A.

(VIII) Sensor guide wire according to embodiment VII, wherein said diameter $D_1$ of said enlargement (22) is between 0.01 and 0.35 mm.

(IX) Sensor guide wire according to any of embodiments VII-VIII, wherein said diameter $D_1$ is larger than a diameter $D_2$ of an intermediate portion (26) of said tip core wire portion (20).

(X) Sensor guide wire according to any of embodiments II-IX, wherein said enlargement (22) is tapering distally along said longitudinal axis A towards said distal tip (21).

(XI) Sensor guide wire according to any of embodiments IX-X, wherein said enlargement (22) is tapering proximally along said longitudinal axis A towards said intermediate portion (26).

(XII) Sensor guide wire according to any of embodiments X-XI, wherein said enlargement (22) has a blunt end.

(XIII) Sensor guide wire according to any of embodiments X-XI, wherein said enlargement (22) is shaped essentially as a truncated cone.

(XIV) Sensor guide wire according to any of embodiments X-XI, wherein said enlargement (22) is shaped essentially as a hemisphere.

(XV) Sensor guide wire according to any of embodiments II-XIV, wherein the length of said enlargement (22) is less than 5 mm, more preferably between 0.2 and 1.6 mm.

(XVI) Sensor guide wire according to any of the preceding embodiments, wherein said polymer layer (23) is radioopaque.

(XVII) Sensor guide wire according to any of embodiments I-XVI, wherein said polymer layer (23) comprises a radioopaque filler.

(XVIII) Sensor guide wire according to embodiment XVII, wherein said polymer layer (23) comprises a polymer with >60 wt % radioopaque filler.

(XIX) Sensor guide wire according to embodiments XVIII, wherein an outer tube (27) is provided that encloses said polymer layer (23).

(XX) Sensor guide wire according to embodiment XIX, wherein said outer tube (27) is a polyolefin, fluoropolymer, or silicone elastomer.

(XXI) Sensor guide wire according to any of embodiments I-XVII, wherein said polymer layer (23) is a hollow polymer tube enclosing said tip core wire portion (20) and extending along said longitudinal axis A in said tip region (12).

(XXII) Sensor guide wire according to embodiment XXI, wherein said polymer tube is heated and formed onto the tip core wire portion (20).

(XXIII) Sensor guide wire according to any of embodiments XXI-XXII, wherein said hollow polymer tube is attached to said tip core wire portion (20).

(XXIV) Sensor guide wire according to any of embodiments I-XXIII, wherein an adhesive material is arranged between said tip core wire portion (20) and said polymer layer (23).

(XXV) Sensor guide wire according to any of embodiments I-XVII, wherein said polymer layer (23) is dip coated onto said tip core wire portion (20).

(XXVI) Sensor guide wire according to any of embodiments I-XVII, wherein said polymer layer (23) is injection moulded onto said tip core wire portion (20).

(XXVII) Sensor guide wire according to any of the preceding embodiments, wherein said polymer layer (23) is an elastic polymer.

(XXVIII) Sensor guide wire according to embodiment XXVII, wherein said polymer layer (23) is silicone.

(XXIX) Sensor guide wire according to embodiment XXVII, wherein said polymer layer (23) is polyurethane.

(XXX) Sensor guide wire according to any of embodiments XVI-XXIX, wherein said polymer layer (23) comprises a ceramic or metal powder such as any of, or a combination of, bismuth, barium, tungsten, tantalum, platinum.

(XXXI) Sensor guide wire according to any of embodiments XVI-XXIX, wherein said polymer layer (23) comprises a nanocomposite hybrid material.

(XXXII) Sensor guide wire according to embodiment XXXI, wherein said nanocomposite hybrid material comprises $Ta_2O_5$.

(XXXIII) Sensor guide wire according to embodiment X, wherein $$\frac{D_1}{D_2} > 1.2.$$

(XXXIV) Sensor guide wire according to any of the preceding embodiments, wherein said sensor guide wire (10) comprises a jacket (16), adapted to enclose at least a part of said sensor element (11), and being provided with at least a first sensor opening (17).

(XXXV) Sensor guide wire according to any of the preceding embodiments, wherein said core wire (18) further comprises a proximal core wire portion (19), extending at least partly along said proximal region (14).

The present invention is not limited to the above-described preferred embodiments. Various alternatives, modifications and equivalents may be used. Therefore, the above embodiments should not be taken as limiting the scope of the invention, which is defined by the appending claims.

What is claimed is:

1. A sensor guide wire for an intravascular measurement of at least one variable in a living body, wherein the sensor guide wire has a proximal region, a distal sensor region and a tip region, the sensor guide wire comprising:
    a sensor element arranged in the sensor region, the sensor element comprising a sensor portion configured to measure the variable and to generate a sensor signal in response to the variable;
    a jacket enclosing at least part of the sensor element, wherein a distal end of the jacket is located distal of the sensor element;
    a core wire comprising at least a tip core wire portion extending along the tip region of the sensor guide wire, wherein the tip core wire portion comprises:
        a first section,
        a second, reduced-diameter section located distal of the first section and having a reduced diameter relative to the first section, and
        a distal tip including an enlarged portion that has a diameter greater than that of the second, reduced-diameter section; and
    a polymer layer disposed directly on the second, reduced-diameter section of the tip core wire portion,
    wherein the first section of the tip core wire portion, the second section of the tip core wire portion, and the distal tip of the tip core wire portion are formed integrally as a single piece;
    wherein a proximal end of the polymer layer extends distally from the distal end of the jacket, and
    wherein a distal end of the polymer layer extends proximally from a proximal end of the enlarged portion of the distal tip.

2. The sensor guide wire according to claim 1, wherein the polymer layer covers at least 75% of an entire length of the tip core wire portion.

3. The sensor guide wire according to claim 1, wherein the polymer layer covers a distal half of the tip core wire portion.

4. The sensor guide wire according to claim 1, wherein the polymer layer covers the entire tip core wire portion.

5. The sensor guide wire according to claim 1, wherein an entire length of the tip core wire portion is between 25 mm and 35 mm.

6. The sensor guide wire according to claim 1, wherein the enlarged portion has a circular cross-section with a diameter in a plane perpendicular to a longitudinal axis of the core wire.

7. The sensor guide wire according to claim 6, wherein the diameter of the enlarged portion is between 0.01 and 0.35 mm.

8. The sensor guide wire according to claim 6, wherein the enlarged portion is tapering distally along the longitudinal axis of the core wire towards the distal tip.

9. The sensor guide wire according to claim 1, wherein $D_1/D_2 > 1.2$ in which $D_1$ is the diameter of the enlarged portion and $D_2$ is the diameter of the second, reduced-diameter portion.

10. The sensor guide wire according to claim 1, wherein the enlarged portion is tapered proximally along the longitudinal axis of the core wire towards the second, reduced-diameter portion.

11. The sensor guide wire according to claim 1, wherein the enlarged portion has a blunt end.

12. The sensor guide wire according to claim 1, wherein the enlarged portion is shaped as a truncated cone.

13. The sensor guide wire according to claim 1, wherein the enlarged portion is shaped as a hemisphere.

14. The sensor guide wire according to claim 1, wherein a length of the enlarged portion is less than 5 mm.

15. The sensor guide wire according to claim 1, wherein the polymer layer comprises a radioopaque filler.

16. The sensor guide wire according to claim 15, wherein the polymer layer comprises a polymer with less than 60 wt % radioopaque filler.

17. The sensor guide wire according to claim 16, further comprising an outer tube enclosing the polymer layer.

18. The sensor guide wire according to claim 17, wherein the outer tube is a polyolefin, fluoropolymer, or silicone elastomer.

19. The sensor guide wire according to claim 1, wherein the polymer layer is a hollow polymer tube enclosing the tip core wire portion and extending along a longitudinal axis of the core wire in the tip region.

20. The sensor guide wire according to claim 19, wherein the polymer tube is heated and formed onto the tip core wire portion.

21. The sensor guide wire according to claim 19, wherein the hollow polymer tube is attached to the tip core wire portion.

22. The sensor guide wire according to claim 1, further comprising an adhesive material arranged between the tip core wire portion and the polymer layer.

23. The sensor guide wire according to claim 1, wherein the polymer layer is dip coated onto the tip core wire portion.

24. The sensor guide wire according to claim 1, wherein the polymer layer is injection molded onto the tip core wire portion.

25. The sensor guide wire according to claim 1, wherein the polymer layer is an elastic polymer.

26. The sensor guide wire according to claim 25, wherein the polymer layer is silicone.

27. The sensor guide wire according to claim 25, wherein the polymer layer is polyurethane.

28. The sensor guide wire according to claim 1, wherein the polymer layer is radioopaque.

29. The sensor guide wire according to claim 28, wherein the polymer layer comprises a ceramic or metal powder.

30. The sensor guide wire according to claim 1, wherein the polymer layer comprises a nanocomposite hybrid material.

31. The sensor guide wire according to claim 30, wherein the nanocomposite hybrid material comprises $Ta_2O_5$.

32. The sensor guide wire according to claim 1, wherein the jacket includes at least a sensor opening.

33. The sensor guide wire according to claim 1, wherein the core wire further comprises a proximal core wire portion extending at least partly along the proximal region.

34. The sensor guide wire according to claim 1, wherein, in a radial direction, the polymer layer extends from an outer surface of the second, reduced-diameter section to at least an outer surface of the first section.

* * * * *